United States Patent [19]

Smith

[11] 4,285,932

[45] Aug. 25, 1981

[54] ENZYME DERIVATIVES FOR USE IN THE TREATMENT OF VENOUS THROMBOSIS

[75] Inventor: Richard A. G. Smith, Dorking, England

[73] Assignee: Beecham Group Limited, England

[21] Appl. No.: 68,205

[22] Filed: Aug. 20, 1979

[30] Foreign Application Priority Data

Sep. 7, 1978 [GB] United Kingdom ............. 35960/78

[51] Int. Cl.³ .................... A61K 37/48; C07C 103/52; C07G 7/00; C12N 9/70; C12N 9/68; C12N 9/99

[52] U.S. Cl. ............................. 424/94; 260/112.5 R; 260/112 R; 435/184; 435/217; 435/216

[58] Field of Search ......................................... 424/94

[56] References Cited

PUBLICATIONS

C. Malen, et al., Chem. Abstr. vol. 76, 1972, p. 85810f.

Z. Skrzydlewski, et al., Chem. Abstr. vol. 78, 1973, p. 699v.

A. J. Baillie, et al., Chem. Abstr. vol. 78, 1973, p. 53467z.

L. Nanninga, Chem. Abstr. vol. 82, 1975, p. 106973c.

T. Chase, Jr., et al., Biochemistry 8, 1969, pp. 2212–2224.

*Primary Examiner*—Delbert R. Phillips
*Attorney, Agent, or Firm*—Jacobs & Jacobs

[57] ABSTRACT

A pharmaceutical composition which comprises a pharmaceutically acceptable carrier together with an in vivo fibrinolytic enzyme as defined herein wherein the catalytic site essential for fibrinolytic activity is blocked by a group which is removable by hydrolysis at a rate such that the pseudo-first order rate constant for hydrolysis is in the range $10^{-6}$ sec$^{-1}$ to $10^{-3}$ sec$^{-1}$ in isotonic aqueous media at pH 7.4 at 37° C.; is useful in the treatment of venous thrombosis.

28 Claims, No Drawings

ENZYME DERIVATIVES FOR USE IN THE TREATMENT OF VENOUS THROMBOSIS

This invention relates to enzyme derivatives for use in the treatment of venous thrombosis.

Venous thrombosis is the formation from the constituents of the blood of a solid mass or plug in a vein. Such plugs or thrombi may be dislodged in whole or in part and may move to another vascular site; when this occurs the thrombus or its fragment is referred to as an embolus. Collectively the states associated with thrombi and emboli are referred to as thromboembolic diseases or disorders, and when viewed together they represent a leading cause of serious illness and death in the Western world.

Currently there are two classes of therapeutic agents proposed for the treatment of venous thrombosis, these are anti-coagulants and thrombolytics. At present anti-coagulants are the most commonly used therapeutic agents; the most widely employed being heparin (generally recognised as most effective) and dihydroxycoumarin (warfarin). The principal disadvantage of anti-coagulant agents is that they have no direct lytic action on the clot and therefore they have little usefulness in the treatment of an acute thrombotic condition. Secondly because they depress the clotting system, a complication inherent in the use of such agents is uncontrollable bleeding, which is recognised as a significant hazard.

Thrombolytic agents suggested to date for use in the treatment of venous thrombosis fall into two classes. Firstly there are proteolytic enzymes which are able to lyse fibrin directly. Secondly there are enzymic activators which activate the lytic pathway in the body liberating plasmin which lyses the clot. Examples of proteolytic enzymes which have been suggested for use as thrombolytic agents include brinase, papain, ochrase, trypsin and plasmin. However these enzymes are extremely toxic because intravenous administration can lead to uncontrolled proteolytic degradation in vivo. For example plasmin degrades fibrinogen and other clotting factors causing a bleeding syndrome. Moreover such agents may cause plasminogen depletion thereby creating a thrombotic state. For these reasons enzymes of this type are rarely used as therapeutic agents.

The two agents generally recognised as most useful for thrombolytic therapy are streptokinase and urokinase. These are activators and operate by converting plasminogen to plasmin. Streptokinase is a secretory product of haemolytic streptococci, and can be produced cheaply in large quantities. Urokinase is available only in very small quantities and is extremely expensive. Although both agents are able to resolve large clots even in deep veins the intense fibrinolytic state which they cause tends to induce bleeding which is again a significant hazard. Consequently the use is strictly limited to patients having a serious thrombotic blockage in a major vein or with pulmonary embolism. Moreover since activators stimulate the natural lytic system their systemic administration can result in plasminogen depletion thus predisposing a patient to a thrombotic state if treatment is prolonged. To some extent this effect may be overcome by the use of streptokinase-plasminogen combinations. This compromise does not present an adequate solution to the problem of therapeutic fibrinolysis since systemic formation of plasmin by such combinations tends to swamp the clotting/lytic pathway control mechanisms. Moreover these combinations do nothing to overcome the problems of uncontrollable bleeding.

We have now discovered that it is possible to overcome most of the disadvantages of known thrombolytic agents by making use of certain enzymes which can be reversibly deactivated. It is recognised that some enzymes such as plasmin or streptokinase/plasminogen activator complex display some selectivity for fibrin particularly in vivo. Although the full structural requirements and characteristics of such enzymes have not been determined, we have devised a test by which enzymes having specificity for fibrin in vivo may be recognised. Hereafter enzymes which are positive in this test will be referred to as "in vivo fibrinolytic enzymes".

We have found that derivatives of these enzymes can be made in which the catalytic activity is masked while the affinity for fibrin remains unaffected, but which will hydrolyse in aqueous media to liberate the active enzyme.

Accordingly the present invention provides a pharmaceutical composition which comprises a pharmaceutically acceptable carrier together with an in vivo fibrinolytic enzyme as defined herein wherein the catalytic site essential for fibrinolytic activity is blocked by a group which is removable by hydrolysis at a rate such that the pseudo-first order rate constant for hydrolysis is in the range $10^{-6}$ sec$^{-1}$ to $10^{-3}$ sec$^{-1}$ in isotonic aqueous media at pH 7.4 at 37° C.

The test used to determine in vivo fibrinolytic activity is performed by forming a radio actively labelled clot in the inferior vena cava in a test rabbit. The agent under test is introduced into the bloodstream at a point where it must pass through the heart to ensure that the agent will be thoroughly mixed with venous blood. Non-specific lytic enzymes attack blood proteins and cause death before any lysis of the clot is observed. Enzymes which have a degree of specificity for fibrin lyse the clot at a dose lower than the lethal dose. The occurrence of lysis is demonstrated by the liberation of radio active fragments into the bloodstream.

By the term "in vivo fibrinolytic enzyme" used in this specification, we mean an enzyme which, when systemically administered in not more than five hours to a rabbit with a radioactively labelled clot localised in its inferior vena cava, will raise the blood radioactivity level to at least twice that of the background level in six hours from beginning the administration, without causing death of the animal.

One specific way of carrying out this test is as follows:

A New Zealand white rabbit (2.5-3.5 kg) is anaesthetised and three cannulas are inserted into the anterior facial vein (referred to as cannula 1 in this description), the left carotid artery (referred to as cannula 2) and the left external iliac vein (referred to as cannula 3). A laparotomy is then performed upon the rabbit to expose the inferior vena cava near its junction with the left renal vein. A section of the inferior vena cava is isolated by closing a ligature near that point and placing a clamp on the inferior vena cava at a point further towards its junction with the left external iliac vein. A radio-labelled clot is induced by injecting 50 μl of a mixture made up of radio-iodinated human fibrinogen (100 μl) and rabbit thromboplastin (150 μl) into the isolated portion of the vein. The quantity of 50 μl is determined arbitrarily, and represents an amount between the minimum quantity which can be measured accurately and the maximum quantity which can be injected without excessive disturbance of physiological conditions within the isolated vein portion. It is essential for the purposes of measuring any radio-activity released into the bloodstream that the amount of radio-activity injected into the vein should be not less than 0.25 $\mu C_i$ and an amount in the range 0.25 to 1.0 $\mu C_i$ is generally convenient. A clot swab is placed over the injecting needle at its point of entry into the exterior wall of the inferior vena cava as the injection is made so as to absorb any seepage from the injection site and any unclotted radio-activity. A second 50 $\mu l$ portion or blank of the fibrinogen-thromboplastin mixture is transferred to a counting vial and its level of $\gamma$-radiation is estimated either by liquid scintillation counting or by direct $\gamma$-counting using a sodium iodide crystal technique. The blank gives a measure of the radio-activity injected into the animal. The first clot swab is kept in place long enough to collect all initial seepage (5 minutes is generally sufficient) and replaced by a second clot swab. The first swab is transferred to a counting vial, and the level of $\gamma$-radiation is measured. The cannula 3 is advanced as far as the aforementioned clamp and 10 minutes following the injection of the fibrinogen-thromboplastin mixture, heparin solution (0.5 ml 500 $\mu$/ml) is administered via cannula 3. The purpose of the heparin injection is to limit the extent of clotting in order to prevent the incorporation of significant amounts of unlabelled endogenous rabbit fibrin into the test clot. The reason for this is that if significant amounts of unlabelled material were incorporated into the clot lysis might go undetected since unlabelled lysis products would be released into the bloodstream. This error would be significant if for example the radio-labelled clot were encapsulated in unlabelled material.

The ligature is partially opened so that the inferior vena cava is constricted to between 40% and 60% of its normal diameter. Constriction is required in order to prevent dislodgement of the clot. The clamp is removed. Heparin solution (1.0 ml, 500 $\mu$ml) is administered via cannula 2 to anti-coagulate the animal and to prevent the formation of clots in addition to that required for the purpose of the experiment. A check is then made for any bleeding which if persistent, is stopped by application of a thrombin-impregnated swab. A blood sample (1.8 ml) is withdrawn via cannula 2 fifteen minutes following the injection of radio-active material and anti-coagulated by adding trisodium citrate buffer (0.2 ml 3.8% w/v). The diluted blood sample ($P_o$) is assayed for $\gamma$-radiation by liquid scintillation counting or direct $\gamma$-counting using a sodium iodide crystal method. This gives a measure of radio-activity in the bloodstream. The clot is then washed by infusion of saline (4.0 ml, 0.2 ml min$^{-1}$) via cannula 3 to wash out any exogenous radio-active material into the circulation and to assist in preventing clot extension by washing away any thrombogenic agents. A second blood sample ($P_{10}$) is withdrawn into citrate buffer as above and counted as previously described ten minutes after $P_o$. This count is made to check that no additional radio-activity has been washed into the bloodstream, thereby giving an indication of the stability of the clot.

Twenty minutes after $P_o$ has been taken, the saline infusion is stopped, a further blood sample is taken (time $t=o$) and the infusion of the test enzyme started. The amount of radiation from the $t=o$ blood sample is a measure of background radiation.

A dose of enzyme is administered by systemic infusion and 2 ml blood samples are taken every 30 minutes for 6 hours following the beginning of the infusion. Each sample is assayed for radio-activity by direct $\gamma$-counting using a sodium iodide crystal method or liquid scintillation counting, and the free plasmin activity are measured ex vivo.

The dose to be administered to the test animal to achieve a positive result is determined by trial and error until activity is observed without causing death. As a guide to the dose to be employed a dose of human plasmin in the range $1 \times 10^{-7}$ to $5 \times 10^{-6}$ mol of active catalytic sites per kg of test animal give a positive result in the test; similarly a dose of streptokinase/plasminogen activator complex is positive in the range $1 \times 10^{-10}$ to $1 \times 10^{-8}$ mol/kg. Accordingly the proteolytic active site concentration is determined, if unknown, either by chromogenic or fluorogenic titration or by determining the molecular weight and specific activity of an analytically pure specimen of the enzyme.

A dose is selected arbitrarily similar to the ranges indicated above. 20% of the selected dose is administered at the onset of the experiment and the remainder is administered over 2 hours. If no activity is observed the experiment is repeated with increasing doses until activity is observed or until toxicity limits the experiment. The period of the infusion may be increased up to 5 hours.

Examples of enzymes which have in vivo fibrinolytic activity as defined herein are urokinase; streptokinase-plasminogen activator complex; vascular activator, particularly human vascular activator and plasmins particularly mammalian plasmins e.g. ovine, porcine, bovine, equine, simian and human plasmin.

Preferred enzymes for use in this invention are human plasmin and the streptokinase/human plasminogen activator complex. We have found that it is particularly advantageous to form a blocked derivative, especially an acyl derivative, of a mixture of human plasmin and streptokinase/human plasminogen activator complex. This mixture is conveniently prepared by activating human plasminogen by means of streptokinase in a conventional manner, and not removing all the activator complex.

We have found that the blocked enzymes employed in the compositions of this invention have the following advantages over the use of the corresponding free enzymes:

(a) they are more efficacious than the free enzyme;

(b) they are longer lasting in terms of their biological activity;

(c) they can be administered as single, often large, intravenous doses because of their relatively low toxicity, whereas in current therapy, enzymes, activators or activator complexes must be given by continual intravenous infusion over periods of several hours or days.

Enzymes such as plasmins may be prepared by known methods as disclosed for example in B.A.K. Chibber et al., Methods in Enzymol., Vol 34 p424–432.; K. C. Robbins and K. Summaria, Methods in Enzymol., Vol. 45 p257–273. Alternatively plasminogen may be isolated by methods disclosed in British Pat. Nos. 1013507, 1066467, 1078141 and 1096953 which may then be converted by standard methods to plasmin.

Human vascular activator may be isolated by the method of D. S. Pepper et al. Progress in Chem. Fibrinolysis and Thrombolysis, 1978, 3., 91–98. Raven Press New York. Streptokinase-plasminogen activator complex is described by D. K. McClintock and P. H. Bell, Bio chem. Biophys Res. Comm. 43, 694–702, 1971. Urokinase may be isolated from human urine as described by T. Macaig et al. Methods in Enzymol Vol. 34 p451–459 and G. H. Barlow Methods in Enzymol Vol. 45 p239–245 Academic Press.

The essential feature of the blocking group for the catalytic site is that it should be removable by hydrolysis at a rate where the pseudo-first order rate constant for hydrolysis is not less than $10^{-6}$ sec$^{-1}$ and not greater than $10^{-3}$ sec$^{-1}$. Preferably the rate constant should be in the range $10^{-5}$ to $10^{-3}$ sec$^{-1}$.

Derivatives having a pseudo-first order rate constant of greater than $10^{-3}$ sec$^{-1}$ liberate unacceptably high levels of free enzyme before attaching to fibrin. Derivatives having pseudo-first order rate constants of less than $10^{-6}$ sec$^{-1}$ liberate enzyme too slowly to be of any clinical use.

The compositions in accordance with this invention may be used as either prophylactic or therapeutic agent. For the purposes of prophylaxis a derivative having a slow rate of hydrolysis and therefore long half life is preferred. Such derivatives suitable for this purposes have pseudo-first order rate constants for hydrolysis in the range $5\times10^{-5}$ to $10^{-5}$ sec$^{-1}$ and half life of 3.5 to 16 hours. For therapeutic purposes a more rapidly hydrolysing derivative is preferred i.e. one having a pseudo-first order rate constant for hydrolysis in the range $5\times10^{-4}$ to $7\times10^{-5}$ sec$^{-1}$ which corresponds to an approximate half life of 30 minutes to 2 hours.

The pseudo-first order rate constant is determined by hydrolysing the enzyme derivative under physiological conditions i.e. in isotonic aqueous media at pH 7.4 and at 37° C. At regular intervals aliquots are withdrawn and incubated with a chromogenic or fluorogenic protease substrate such as S-2251 (H-D-Val-Leu-Lys-p-nitroanilide 2HCl) and the rate of conversion of the substrate measured.

The hydrolysis is followed until such time as the rate of conversion of substrate reaches a maximum. The rate constant k is then calculated by plotting:

$$\log_e (1 - A_t/A_{max}) \text{ against } t$$

where $A_{max}$ the maximum rate at which an aliquot converts substrate and $A_t$ is the rate at which an aliquot converts substrate at time t.

The precise identity of the blocking group used in the derivatives of this invention depends to a degree on the nature of the enzyme selected and the use to which the derivative will be put.

In the case of plasmin and the streptokinase/plasminogen activator, for example, the catalytic site essential for proteolytic activity includes a serine residue having a free hydroxyl moiety. The site is conveniently blocked by acyl groups such as benzoyl, substituted benzoyl, acryloyl or substituted acryloyl groups. The pseudo-first order rate constant for hydrolysis of any particular substituted benzoyl enzyme derivative can be estimated on the basis of the Hammett $\sigma$ value of any substituent once the pseudo-first order rate constant of two or more substituted benzoyl derivatives have been measured provided that there is no special interaction between a particular substituent and the enzyme.

It is generally recognised that Hammett values for meta and para substituents ($\sigma_m$ and $\sigma_p$) give an acceptable prediction of hydrolysis rates. Moreover $\sigma_m$ and $\sigma_p$ values may be summed with reasonable accuracy to calculate kinetic properties of other substituted benzoyl groups bearing more than one substituent. Hammett values for ortho substituents ($\sigma_o$) cannot be summed with the same reliability as $\sigma_m$ and $\sigma_p$ values because of steric effects. However when the ortho substituent is small and therefore produces a negligible steric effect i.e. in the case of fluorine, methyl and methoxy, then the $\sigma_o$ value may within generally accepted degrees of error be used alone or summed with $\sigma_m$ and/or $\sigma_p$ values to calculate reaction rates.

Subject to these limitations, a substituted benzoyl group in which the phenyl ring bears one or more substituents, particularly meta and/or para substituents where the sum of the Hammett $\sigma$ values is in the range 0.1 to −1.1 may be used in accordance with this invention to block human plasmin. A substituted benzoyl group in which the phenyl ring bears one or more substituents particularly meta and/or para substituents such that the sum of the Hammett $\sigma$ values is in the range −0.9 to +0.3 may be used in accordance with this invention to block the catalytic site of porcine plasmin.

Suitable benzoyl and substituted benzoyl groups include benzoyl, optionally substituted with halogen, $C_{1-6}$ alkyl $C_{1-6}$ alkoxy, $C_{1-6}$ alkanoyloxy, $C_{1-6}$ alkanoylamino (RCOHN-). Examples include, benzoyl, p-fluorobenzoyl, o-, m-, or p-toluoyl, o-, m-, or p-methoxybenzoyl (i.e. anisoyl), o-, m-, or p-ethoxybenzoyl, 2,4-dimethoxybenzoyl, 3,4-dimethylbenzoyl, 4-butylbenzoyl, 3-methyl-4-methoxybenzoyl, o-acetoxybenzoyl (i.e. acetylsalicyloyl) and p-acetamidobenzoyl. A further aromatic group is naphthoyl.

The exception to this general rule is where the benzoyl group contains a basic moiety such as amino, dimethylamino and guanidino. The rate of hydrolysis of such derivatives is up to ten times less rapid than the calculated value.

Examples of such derivatives are p-guanidinobenzoyl human and porcine plasmin.

Another series of acyl groups which may be used to block human and porcine plasmins in accordance with the invention are acryloyl and substituted acryloyl, in particular cinnamoyl and substituted cinnamoyl groups bearing one or more substituents particularly meta and/or para substituents in which the sum of the Hammett $\sigma$ values is in the range −1.0 to +0.15 subject to the limitations above.

Suitable substituted acryloyl groups $C_{1-6}$ alkylacryloyl, furyl-acryloyl, cinnamoyl, $C_{1-6}$ alkyl-cinnamoyl. Specific examples include 3,3-dimethylacryloyl, 2-furyl-3-acryloyl, cinnamoyl, and p-methylcinnamoyl.

The compositions according to this invention are formulated in accordance with routine procedures as pharmaceutical compositions adapted for intravenous administration to human beings.

Typically compositions for intravenous administration are solutions of the sterile derivative in sterile isotonic aqueous buffer. Where necessary the composition may also include a solubilizing agent to keep the derivative in solution and a local anaesthetic siuch as lignocaine to ease pain at the site of injection. Generally, the enzyme derivative will be supplied in unit dosage form for example as a dry powder or water free concentrate in a hermetically sealed container such as an ampoule or sachette indicating the quantity of enzyme in activity units, as well as an indication of the time within which the free enzyme will be liberated. Where the derivative is to be administered by infusion, the derivative will be dispensed with an infusion bottle containing sterile pharmaceutical grade "Water for Injection". Where the derivative is to be administered by injection the derivative is dispensed with an ampoule of sterile water for injection. The injectable or infusable composition will be made up by mixing the ingredients prior to administration.

The quantity of material administered will depend upon the amount of fibrinolysis required and the speed with which it is required, the seriousness of the thromboembolic condition and the position and size of the clot. For example a patient with a pulmonary embolism or a large life threatening ascending ileo-femoral thrombus will require administration of a bolus of rapidly acting material. On the other hand where it is desired to prevent the formation of post-operative thrombi, a small quantity of slow acting material will be required. The precise dose to be employed and mode of administration must per force in view of the nature of the complaint be decided according to the circumstances by the physician supervising treatment. However, in general, a patient being treated for a medium size thrombus will generally receive a daily dose of from 1 to 20 mg kg$^{-1}$ of body weight either by injection in up to eight doses or by infusion.

A number of derivatives which may be used in the compositions of this invention are known. These appear below together with a literature reference reporting their preparation:

1. p-Guanidinobenzoyl human plasmin, T. Chase and E. Shaw, Biochem., 8, No. 5, 2212-2224, 1969.

2. p-Guanidinobenzoyl streptokinase-plasminogen activator complex, D. K. McClintock and P. H. Bell, Biochem. Biophys. Res. Comm. 43, 694-702, 1971.

In the past these two derivatives have been formed during active-site titrations of the above enzymes. The isolation and characterization of these derivatives has never been reported. Moreover it has never previously been recognised that these enzyme derivatives are useful as fibrinolytic agents.

Accordingly in a further aspect the invention provides an isolated derivative of an in vivo fibrinolytic enzyme as defined herein wherein the catalytic site essential for fibrinolytic activity is blocked by a group which is removable by hydrolysis such that the pseudo first order rate constant for hydrolysis of the derivative is in the range $10^{-6}$ sec$^{-1}$ to $10^{-3}$ sec$^{-1}$ in isotonic aqueous media at pH 7.4 at 37° C.

In yet a further aspect the invention provides a derivative of an in vivo fibrinolytic enzyme as defined herein wherein the catalytic site essential for fibrinolytic activity is blocked by a group which is removable by hydrolysis such that the pseudo-first order rate constant for hydrolysis of the derivative is in the range $10^{-6}$ sec$^{-1}$ to $10^{-3}$ sec$^{-1}$ in isotonic aqueous media at pH 7.4 at 37° C. with the exception of:

(1) p-guanidinobenzoyl human plasmin.

(2) p-guanidinobenzoyl streptokinase-plasminogen activator complex.

The derivatives of this invention may be prepared in two ways, i.e. by direct or inverse blocking.

The direct blocking method involves reacting the enzyme with an agent:

AB in which A is a group which is selective for the catalytic site essential for fibrinolytic activity and which is capable of transferring from the group B to the catalytic site and B is a leaving group which facilitates the attachment of the enzyme by A; and thereafter optionally isolating the enzyme derivative so formed.

Agents which operate in this way are known. One example is p-nitrophenyl p'guanidinobenzoate. The guanidinobenzyl moiety becomes selectively situated adjacent the catalytic site and its attachment is assisted by the p-nitrophenyl leaving group. The inverse blocking method involves the use of an agent

EF where E is a locating group which locates the agent in the catalytic site and F is a group which is capable of transferring from the locating group to the catalytic site, and thereafter optionally isolating the derivative so formed.

Examples of the group E, when the enzyme to be blocked is plasmin or streptokinase/plasminogen activator include p-amidinophenyl and p-acetamidinophenyl or structurally similar substituted phenyl groups containing a positively charged moiety in the meta or para position.

Examples of inverse blocking agents are: p-amidinophenyl p'fluorobenzoate, p-amidinophenyl p'-toluate, p-amidinophenyl p'anisate, p-amidinophenyl benzoate, p-amidinophenyl cinnamate, p-amidinophenyl p'-methylcinnamate, p-amidinophenyl 3-(2-furyl)-acrylate, p-amidinophenyl 2-naphthoate, p-amidinophenyl 3,3-dimethylacrylate, p-amidinophenyl 4-butyl benzoate, p-amidinophenyl 2,4-dimethoxybenzoate, p-amidinophenyl acetylsalicylate, p-amidinophenyl 4-ethoxybenzoate, p-acetamidinophenyl p'-anisate, p-amidinophenyl o-toluate, p-amidinophenyl o-anisate, p-amidinophenyl 3,4-dimethylbenzoate, p-amidinophenyl 3-methyl-4-methoxy benzoate, and p-amidinophenyl 4-acetamidobenzoate.

The direct and inverse blocking reactions are carried out in aqueous media at a pH range which is not detrimental to the enzyme, blocking agent or product, e.g. between pH 4 and 8 and preferably at a pH in the range 5.0 to 7.5.

The reaction is generally carried out using equi-molar equivalents of enzyme and blocking agent, but excess of blocking agent may be employed. It is also preferred to carry out the reaction in dilute solution, i.e. less than $10^{-3}$ molar with respect to enzyme and less than $10^{-2}$ molar with respect to blocking agent. Generally the reaction will not be carried out in a solution where the concentration of enzyme or blocking agent is less than $10^{-7}$ molar.

The blocking reaction should be carried out at moderate temperatures, i.e. room temperature or below, and more particularly less than 10° C. but greater than the freezing point of the reaction medium.

The time for which the reaction is allowed to proceed depends upon the blocking reagent employed, the temperature at which the reaction is carried out and the enzyme selected for blocking. The optimum time period for any particular circumstances may be selected by following the decrease in enzymic activity by incubating aliquots with a chromogenic or fluorogenic substrate.

After the reaction is complete the derivative is purified by standard methods such as dialysis, affinity chromatography, and ultra filtration, and thereafter recovered by standard methods such as freeze drying from aqueous media. Where necessary the material may be adapted for example by sterilization for intravenous administration to human beings.

The inverse blocking agents:

EF where E is p-amidinophenoxy and F is an acyl group may be prepared by acylating p-hydroxybenzamidine or a salt thereof with an acylating derivative:

FX wherein F is as previously defined and X is hydroxyl or an activated acylating derivative thereof, optionally in the presence of a catalyst.

Examples of activated acylating derivatives include the acyl chloride or bromide. These derivatives may be prepared by standard methods.

Suitable catalysts for this process include tertiary organic bases such as pyridine and condensation promoting agents such as dicyclohexylcarbodiimide.

The acylation reaction is generally carried out in a polar organic solvent which is inert to the reagents and product. Examples of suitable solvents include N,N-dimethylformamide and dimethylsulphoxide. Alternatively where the catalyst is a liquid as in the case of pyridine then the reaction may be carried out in the absence of solvent.

The reaction is generally carried out at moderate temperatures i.e. less than 70° C. and generally less than 40° C.; ambient temperature is most convenient.

The time for the reaction to proceed to completion depends upon the specific reagents employed, the solvent and the temperature at which the reaction is performed. This may be determined by following the reaction for example by thin layer chromatography.

When the reaction is complete, the product is recovered and purified by standard methods.

Inverse blocking agents where E is a substituted benzoyl group are novel and form a further aspect of the invention.

The following examples illustrate the invention.
Examples 1–7 illustrate the preparation of inverse blocking agents.

EXAMPLE 1

Benzoic Acid p-Amidinophenyl Ester. HCl p-Hydroxybenzamidine. HCl (0.172 g) was dissolved in dry pyridine (1.0 ml) and a solution of benzoyl chloride 0.141 g) in pyridine (1.0 ml) added dropwise. The mixture was stirred for 1 hour at ambient temperature and allowed to stand for 4 days also at ambient temperature. The material was evaporated to near dryness, triturated with dry diethyl ether and the solid recrystallised from 2-propanol/diethyl ether 2:1 v/v (c. 3 ml). Yield 0.223 g. M.P. 160° C.

N.M.R. δ(Dimethylsulphoxide d$^6$): 9.65. Doublet. 4$\underline{H}$. Exchangeable with D$_2$O. Amidine H.: c. 8.0. Multiplet. 9$\underline{H}$. Phenyl and Amidinophenyl.

The compounds of Examples 2 to 10 were prepared in similar manner to the method described in Example 1.

EXAMPLE 2

Trans-Cinnamic Acid p-Amidinophenyl Ester. HCl

M.P. 192° C.

N.M.R. δ(Dimethylsulphoxide d$^6$): 9.55 Doublet 4$\underline{H}$. Exchangeable with D$_2$O. Amidine H.: 7.95. Multiplet. 6$\underline{H}$. Amidinophenyl and acryloyl H.: 7.10. Multiplet 5H. Phenyl H.: 6.96. Doublet (J: 16 Hz) 1$\underline{H}$. Acryloyl H.

EXAMPLE 3 p-Anisic Acid p'-Amidinophenyl Ester. HCl

Recrystallised from 2-propanol. M.P. 225° C.

N.M.R. δ(Dimethylsulphoxide d$^6$): 9.50. Doublet. 4$\underline{H}$. Amidinophenyl H.: 7.38. Quartet. (J: 9 Hz) 4$\underline{H}$. p-Anisoyl H.: 3.90. Singlet 3$\underline{H}$. Methoxy H.

EXAMPLE 4

3,3Dimethylacrylic Acid p-Amidinophenyl Ester Hydrochloride

Recrystallised from water. M.P. 173° C. N.M.R. δ(Dimethylsulphoxide d$^6$). 9.50 doublet 4$\underline{H}$ exchangeable with D$_2$O, amidine H; 7.95 and 7.37 quartet (J=9 Hz) 4$\underline{H}$, amidinophenyl H; 5.96$^2$ broad doublet (J=1 Hz) 1$\underline{H}$, acryloyl H; 2.09 singlet 3$\underline{H}$, methyl H; 1.90 singlet 3$\underline{H}$ methyl H.

EXAMPLE 5

4-Butyl Benzoic Acid p-Amidinophenyl Ester Hydrochloride

Recrystallised from isopropanol/water. (1:4 v/v). M.P. 190° C. N.M.R. δ(dimethylsulphoxide d$^6$). 9.55 broad doublet 4$\underline{H}$ exchangeable with D$_2$O, amidine H. 7.60 8.1 overlapping quartets 5$\underline{H}$ amidinophenyl+benzoyl H. 1.30 singlet 9$\underline{H}$ ε-butyl H.

EXAMPLE 6

2,4-Dimethoxybenzoic Acid p-Amidinophenyl Ester Hydrochloride

Recrystallised from methanol, M.P. 213°–4° C. N.M.R. δ(Dimethylsulphoxide d$^6$): 9.48 doublet 4$\underline{H}$ exchangeable with D$_2$O, amidine H; 8.01 and 7.50 AA'BB' quartet (J: 8 Hz) 4$\underline{H}$, amidinophenyl H; 8.03 and 6.75 multiplet 3H, 2,4 substituted phenyl H; 3.90 singlet 6$\underline{H}$, 2× methoxy H.

EXAMPLE 7

Acetyl Salicyclic Acid p-Amidinophenyl Ester Hydrochloride

Recrystallised from isopropanol, M.P. 109°–111° C. N.M.R. δ(Dimethylsulphoxide d$^6$): 9.62 broad doublet 4$\underline{H}$ exchangeable with D$_2$O, amidine H; 8.12 and 7.55 AA'BB' quartet (J: 9 Hz) 4$\underline{H}$, amidinophenyl H; 2.26 singlet 3$\underline{H}$, acetyl H.

EXAMPLE 8

4-Ethoxybenzoic Acid p-Amidinophenyl Ester Hydrochloride

Recrystallized from isopropanol, M.P. 211°–2° C. N.M.R. δ(Dimethylsulphoxide d$^6$): 9.60 broad doublet 4$\underline{H}$ exchangeable with D$_2$O amidine H; 8.10 and 7.56 AA'BB' quartet (J: 9 Hz) 4$\underline{H}$, amidinophenyl H; 8.13 and 7.15 AA'BB' quartet (J: 9 Hz) 4$\underline{H}$, 4-ethoxyphenyl H; 4.19 quartet 2H, —O$\underline{CH_2}$CH$_3$; 9.38 triplet 3$\underline{H}$, —OCH$_2$$\underline{CH_3}$.

EXAMPLE 9

O-Toluic Acid p-Amidinophenyl Ester Hydrochloride

Twice recrystallised from isopropanol/diethyl ether. M.P. 157°–9° C. N.M.R. δ(Dimethylsulphoxide d$^6$): broad doublet 4H exchangeable with D$_2$O, amidine H;

8.20 and 7.62 AA'BB' quartet 4H, amidinophenyl H; 7.3–8.2 multiplet 4H, 2-methylphenyl H; 2.11 singlet 3H, methyl H.

EXAMPLE 10

(a) 2-(4-Hydroxyphenyl) Acetamidine Hydrochloride p-Hydroxybenzyl cyanide (5.0 g) was dissolved in absolute ethanol (50 ml) and the solution saturated with dry HCl gas over 4 hours at ambient temperature. After standing at 4° C. for 72 hours, dry diethyl ether (200 ml) and light petroleum (100 ml) were added and white crystals were deposited over 2 hours. The solid was isolated by filtration and reacted immediately with saturated ethanolic ammonia (300 ml) for 3 hours at ambient temperature. The reaction mixture was evaporated to dryness on a steam bath and the residue recrystallised from ethanol. Yield 4.36 g M.P. 248° C. (dec.) N.M.R. δ(Dimethylsulphoxide $d^6$) 9.0–9.8 envelope 5H exchangeable with D$_2$O, amidine H, hydroxyl H. 6.85+7.37 AA'BB' quartet 4H (J: 9 Hz) phenyl H; 3.70 singlet 2H benzyl H.

(b) 4-Methoxybenzoic Acid p-Acetamidinophenyl Ester Hydrochloride

Recrystallised from isopropanol/diethyl ether. M.P. 174°–6° C. N.M.R. δ(Dimethylsulphoxide $d^6$): 9.42 broad doublet 4H exchangeable with D$_2$O, amidine H; 8.15 and 6.29 AA'BB' quartet (J: 8 Hz) 4H, 4-methoxyphenyl H; 7.69 and 7.13 AA'BB' quartet (J: 8 Hz) 4H, amidinophenyl H; 3.90 singlet 3H, methoxy H.

EXAMPLE 11 p-Toluic Acid p'Amidinophenyl Ester. HCl p-Hydroxybenzamidine HCl (1.72 g) and p-toluic acid (1.36 g) were dissolved in a mixture of dry pyridine (5.0 ml) and dimethylsulphoxide (10.0 ml) and stirred with N,N Dicyclohexyl carbodiimide (2.1 g) for 72 hours at ambient temperature. The product was filtered and the filtrate precipitated with dry diethyl ether (200 ml). The resulting oil crystallised after precipitation and was recrystallised from 2-propanol/1,4 dioxane 1:1 v/v. M.P. 164° C.

N.M.R. δ(Dimethylsulphoxide $d^6$): 9.6 Broad Doublet exchangeable with D$_2$O. 4H. Amidine H.: 8.15 Quartet (J: c. 4 Hz) 4H. Amidinophenyl H.: 7.60 Quartet (J: c. 9 Hz) 4H. Benzoyl H.: 2.44 Singlet 3H. Methyl H. The compounds of Examples 12 to 18 were prepared by the method described in Example 11.

EXAMPLE 12 p-Fluorobenzoic Acid p'Amidinophenyl Ester Perchlorate

Ether-precipitated oil recrystallised from 5% w/v perchloric acid (10 ml). M.P. 180° C. (Decomp)

N.M.R. δ(Dimethylsulphoxide $d^6$).: 9.3 Doublet 4H. exchangeable with D$_2$O. Amidine H.: 8.25 Quartet (J: c. 5 Hz) 2H. 3,5H in benzoyl.: 7.8 Overlapping quartets 6H. Amidinophenyl H and 2.6H in benzoyl.

EXAMPLE 13

3-(2-Furyl) Acrylic Acid p-Amidinophenyl Ester Perchlorate

Coupling performed in pyridine. Filtrate evaporated to near dryness and residue recrystallised from dilute perchloric acid. Off-white plates M.P. 157° C.

N.M.R. δ(Dimethylsulphoxide $d^6$): 9.35 Doublet exchangeable with D$_2$O 4H Amidine H.: 7.7 Quartet (J: c. 8 Hz) 4H. Amidinophenyl H.: 7.9 Doublet (J: c. 3 Hz) 1H 5-Furyl H.: 7.85/7.40 Doublet (J: 20 Hz) 1H. 2-Acryloyl H.: 7.10 Doublet (J: c. 3 Hz) 1H. 3-Furyl H.: 6.70 Multiplet. 1H 4-Furyl H.: 6.44 Doublet (J: 15 Hz) 1H 3-Acryloyl H.

EXAMPLE 14 p-Methyl-Trans-Cinnamic Acid p-Amidinophenyl Ester Perchlorate

Isolated as for 3-(2-Furyl) acrylic acid ester. M.P. 155° C.

N.M.R. δ(Dimethylsulphoxide $d^6$): 9.15 Doublet exchangeable with D$_2$O. 4H. Amidine H.: 7.2–8.2 Multiplet 9H. Amidinophenyl and phenyl H.: 6.82 Doublet (J: 16 Hz) 1H 2-acryloyl H.: 6.44 Doublet (J: 16 Hz) 1H. Acryloyl H.: 2.42 Doublet (J: 2 Hz) 3H. Methyl H.

EXAMPLE 15

O-Anisic Acid p-Amidinophenyl Ester Hydrochloride

Recrystallised from isopropanol. M.P. 149° C. N.M.R. δ(Dimethylsulphoxide $d^6$) 9.50 broad singlet 4H exchangeable with D$_2$O, amidine H; 7.50 and 7.95 irregular multiplet 5H, amidinophenyl H and 2-H; 7.0–7.5 multiplet 3H 3,4,5 benzoyl H; 3.86 singlet 3H methoxy H.

EXAMPLE 16

3,4 Dimethyl Benzoic Acid p-Amidinophenyl Ester Hydrochloride

Recrystallised from isopropanol/brine M.P. 107° C. N.M.R. δ(Dimethylsulphoxide $d^6$) 9.56 broad singlet 4H exchangeable with D$_2$O, amidine H; 7.50–7.95 irregular triplets 7H amidinophenyl and benzoyl H. 2.30 singlet 6H methyl H.

EXAMPLE 17

3,Methyl-4-Methoxy Benzoic Acid p-Amidinophenyl Ester Hydrochloride

Recrystallised from isopropanol/2 N HCl (10:1 v/v). M.P. 210° C. N.M.R. δ(Dimethylsulphoxide $d^6$). 9.54 doublet 4H exchangeable with D$_2$O, amidine H. 8.07 irregular doublet 4H. 2-H+6-H benzoyl, 2H, 6H amidinophenyl; 7.60 doublet (J=9 Hz) 2H, 3H, 5H amidinophenyl; 7.22 doublet (J=9 Hz) 1H 5H benzoyl; 3.92 singlet 3H methoxyl H; 2.26 singlet 3H methyl H.

EXAMPLE 18

4-Acetamidobenzoic Acid p-Amidinophenyl Ester Hydrochloride

Recrystallised from isopropanol/water 1:2 v/v. M.P. 257° C. N.M.R. δ(Dimethylsulphoxide $d^6$) 10.62 singlet 1H exchangeable with D$_2$O, amidine H. 7.90 AA'BB' quartet 4H overlapping 7.50–7.9 AA'BB' quartet 4H, benzoyl and amidinophenyl H. 2.09 singlet 3H, acetyl H.

EXAMPLE 19

Isolated Freeze-Dried p-Anisoyl Human Plasmin

Human plasmin (0.15 micromoles) in 20% v/v glycerol/0.9% w/v saline solution (4.2 ml) was treated with 50 microliters of a 0.1 M solution of p-amidinophenyl p'anisate (prepared as in Example 3 above) in dimethylsulphoxide at 22° C. After 7.5 minutes a further 50 microliters of acylating agent were added. The product was dialysed for 2 hours against 2 liters of the above glycerol/saline mixture and then added to a mixture of L-Lysine-Sepharose 4B (Pharmacia Fine Chemicals, 23 grams wet weight) and 0.1 M Triethanolamine Hydrochloride buffer pH 7.0 (20 ml). The mixture was incubated for 10 minutes at 4° C., and then filtered the gel being washed with 100 ml of the above buffer. The gel was then mixed with a solution of ε-aminocaproic acid 0.2 M in the above buffer and incubated at 4° C. for 10 minutes. After filtration and washing with another 55 ml of the ε-aminocaproic acid solution., the filtrate was dialysed against two changes of 50 mM ammonium bicarbonate buffer pH 7.0 (5 liters) at 4° C. for two hours. The final retentate was mixed with Dextran T 70 (Pharmacia) and freeze-dried. 1.98 g of a white solid resulted. This inactivated material could be reactivated quantitatively to free plasmin in approximately two hours under the conditions specified for deacylation.

The acylating agents of Examples 1, 2 and 4 to 18 were also reacted with human plasmin by the method of Example 19 to give the corresponding blocked plasmin. With the acylating agent of Example 10, it is preferable to use a higher concentration of the acylating agent or allow the reaction to proceed a longer time to ensure complete reaction. The deacylation rates of the latter compounds are gven in table 1 below.

EXAMPLE 20

Freeze-Dried p-Guanidinobenzoyl Human Plasmin

Human plasmin (8.45 nanomoles) in 20% v/v glycerol (1.0 ml) was treated twice with 10 microliters of 0.1 M p-nitrophenyl p'guanidinobenzoate in dimethylsulphoxide for 10 minutes at 0° C. The solution was adjusted to pH 6.0 with dilute hydrochloric acid and dialysed for 2 hours against 2 liters of 10 mM ammonium bicarbonate buffer pH 7.0. L-Lysine. HCl (100 milligrams) was added and the mixture freeze dried. A pale yellow solid (93.5 milligrams) was isolated which could be hydrolysed to active plasmin.

EXAMPLE 21

Preparation of a Solution of Trans-Cinnamoyl Porcine Plasmin

Porcine plasmin (1.73 micromoles) in 10% v/v glycerol 0.9% w/v saline solution (26 ml) was treated with p-amidinophenyl transcinnamate (3.02 milligrams) suspended in 0.9% w/v saline (1 ml) by stirring for 20 minutes at 4° C. The mixture was then frozen at −20° C. and stored at this temperature overnight. After thawing, the mixture was dialysed in the above glycerol/saline mixture (2 liters) at 4° C. for 2 hours. The product was stored at 0° C. until used. The derivative had less than 0.5% of the activity of the original enzyme and could be reactivated in two hours under deacylation conditions.

EXAMPLE 22

Preparation of a Solution of p-Anisoyl Streptokinase-Human Plasminogen Activator Complex Streptokinase (5×10⁴ units, A. B. Kabi, Stockholm, Sweden) in 0.9% w/v saline solution 10.5 ml) was mixed with lys-human plasminogen (0.025 ml 4.9 nanomoles). The mixture was incubated at 25° C. for 40 minutes and then diluted with 0.1 M Trishydroxymethylaminomethan hydrochloride, 0.9% w/v saline 20% v/v glycerol pH 7.4 (2.0 ml). This solution was treated with 3 lots of 0.1 mM (final concentration) p-amidinophenyl p'anisate (prepared as a stock solution 0.1 M in dimethylsulphoxide) for 3 five minute periods at 25° C. The acylated enzyme was mixed with a 33% wet wt/vol suspension of L-lysine sepharose 4B (2.5 ml) for 10 minutes at 0° C. The suspension was filtered under suction and washed with the above Tris/glycerol/saline buffer (100 ml) at 4° C. The gel was re-suspended in the Tris/glycerol/saline buffer (5 ml) containing, in addition, 0.1 M-aminocaproic acid. After 10 minutes at 0° C., the suspension of gel was clarified by centrifugation for 2 minutes at 1000 g and the supernatant (4 ml) dialysed against the Tris/glycerol/saline buffer (2.0 l) at 4° C. for 2 hours. The resulting solution of acyl-activator complex could be regenerated to free enzyme at 37° C. with a pseudo-first order rate constant of $2.7 \times 10^{-4} \sec^{-1}$.

EXAMPLE 23

Preparation of a Solution of 3-Methyl p-Anisoyl Streptokinase-human Plasminogen Activator Complex This material was prepared in the same way as described in Example 22 except that the acylation was performed with 2 lots of 0.2 mM (final concentration) of 3-Methyl p-anisic acid p-amidinophenyl ester in 2 periods of 15 minutes at 25° C., followed by 1 hour at 0° C. The pseudo-first order deacylation rate constant was $1 \times 10^{-4} \sec^{-1}$.

EXAMPLE 24

Preparation of a Mixture of p-Anisoyl Human Plasmin and p-Anisoyl Streptokinase-Human Plasminogen Activator Complex Lys-human plasminogen (216 mg, 2.56 micromoles dissolved to concentration of 6.8 mg/ml in 0.1 M Trishydroxymethylaminomethane hydrochloride, 0.9% w/v saline, 20% v/v glycerol pH 7.4 was treated with streptokinase (A. B. Kabi, Sweden 1.2×10⁴ units, approximately 2.67 nanomoles). The mixture was incubated at 25° C. for 1 hour and bought to 33% v/v glycerol. This solution (9.0 ml) was acylated with 2 lots of 0.1 mM (final concentration) p-amidinophenyl p-anisate in 2 periods of 15 minutes at 25° C. and then dialysed for 1 hour against 2 liters of the above buffer. The resulting solution showed less than 1% of the original plasmin activity and was in a form suitable for use in the rabbit test system.

EXAMPLE 25

Stoichiometric Reaction of (³H-Methoxy)-p-Amidinophenyl p'Anisate with Human and Porcine Plasmins (a) Human Plasmin Solutions of human plasmin ($2.67 \times 10^{-5}$ M, 0.2 ml 5.34 nanomoles) were reacted with 2 lots of a 20 mM solution of tritiated p-amidinophenyl p-anisate (specific radioactivity: 22.8 mC$_i$/m mole) in two 7.5 minute periods at 25° C. After addition of 10% w/v trichloracetic acid in acetone (1.8 ml), the protein was precipitated and isolated by centrifugation at 1500 g for 3 minutes. The protein pellet was washed with two lots of acid-/acetone (2 ml) and dissolved in 2 N sodium hydroxide solution (1.0 ml). Liquid scintillation counting of this solution showed a mean 0.130 μCi associated with protein, corresponding to 5.73 nanomoles of anisic acid.

(b) Porcine Plasmin

A similar experiment using a solution of pig plasmin ($5.29 \times 10^{-5}$ M 10.54 nanomoles used) gave a mean radiochemical analysis for anisic acid of 9.58 nanomoles.

EXAMPLE 26

Freeze-Dried p-Anisoyl Streptokinase-Human Plasminogen Activator Complex

Streptokinase ($9 \times 10^4$ units) in 0.9% w/v saline solution (0.9 ml) was mixed with lys-human plasminogen (0.075 ml 14.9 nanomoles). The mixture was incubated at 25° C. for 30 minutes and then diluted with 0.1 M Trishydroxymethylaminomethane hydrochloride pH 7.4 (4.0 ml). This solution was treated with 3 lots of 0.1 mM (final concentration) p-amidinophenyl p-anisate (prepared as a stock solution 10 mM in dimethylsulphoxide) for 3 five minute periods at 25° C. The acylated enzyme was mixed with a 33% wet wt/vol suspension of L-lysine Sepharose 4B (5.0 ml) for 10 minutes at 0° C. The suspension was filtered under suction and washed with the above TrisHCl buffer (200 ml) at 4° C. The gel was re-suspended in 0.1 M-aminocaproic acid, 50 mM TrisHCl pH 7.4 (5.0 ml) and then filtered, washing with 3 five ml lots of the same buffer. The combined eluate was dialysed against 2 liters of 5% w/v Mannitol in TrisHCl buffer (5.0 mM) pH 7.4 for 2 hours at 4° C. and then freeze-dried to a white powder. (0.560 g). This material had less than 5% of the original enzyme activity and could be regenerated in aqueous media at 37° C.

Hydrolysis Data

The pseudo-first order rate constants (K) for enzyme derivatives prepared from the acylating agents described in Examples 1 to 18 are given in table 1 below.

TABLE 1

Deacylation Rates of Active Site Serine Substituted Plasmins pH 7.4, 37° C.

| Acyl Group | Human Plasmin K sec$^{-1} \times 10^4$ | Porcine Plasmin K sec$^{-1} \times 10^4$ |
|---|---|---|
| p-Fluorobenzoyl | — | 3.30 |
| Benzoyl | 5.20 | 1.90 |
| p-Toluoyl | 2.30 | 0.74 |
| p-Anisoyl | 1.10 | 0.33 |
| Trans-cinnamoyl | — | 4.20 |
| p-Methyl-t-cinnamoyl | — | 2.92 |
| 3-(2-Furyl) acryloyl | 1.33 | 1.50 |
| p-Guanidinobenzoyl | 0.41 | 0.21 |
| N-methyl-p-guanidinobenzoyl | 2.0 | — |
| O-Anisoyl | 1.82 | — |
| p-Acetamidobenzoyl | 2.70 | — |
| Acetylsalicycloyl | 4.70 | — |
| 3,3 Dimethylacryloyl | 0.69 | — |
| 3,4 Dimethylbenzoyl | 0.55 | — |
| 3 Methyl 4-methoxybenzoyl | 0.70 | — |
| O-Toloyl | 1.71 | — |
| p-Ethoxybenzoyl | 1.10 | — |
| 2,4 Dimethoxybenzoyl | 1.10 | — |

I claim:

1. A pharmaceutical composition for treatment of Venous thrombosis which comprises a pharmaceutically acceptable carrier together with an in vivo fibrinolytic enzyme as defined herein wherein the catalytic site essential for fibrinolytic activity is blocked by a group which is removable by hydrolysis at a rate such that the pseudo-first order rate constant for hydrolysis is in the range $10^{-6}$ sec$^{-1}$ to $10^{-3}$ sec$^{-1}$ in isotonic aqueous media at pH 7.4 at 37° C.

2. A pharmaceutical composition for the prophylactic or therapeutic treatment of venous thrombosis comprising a pharmaceutically acceptable carrier together with an in vivo fibrinolytic enzyme which can be reversibly deactivated and a blocking acyl group removable by hydrolysis at a rate defined by claim 1.

3. A pharmaceutical composition according to claim 2, wherein the enzyme is urokinase, streptokinase-plasminogen activator complex, vascular activator and mammalian plasmins.

4. A composition as claimed in claim 1 wherein the enzyme is human plasmin.

5. A composition as claimed in claim 1 wherein the enzyme is streptokinase/human plasminogen activator complex.

6. A composition as claimed in claim 1 wherein the enzyme is a mixture of human plasmin and streptokinase/human plasminogen activator complex.

7. A composition as claimed in claim 1 wherein the group which is removable by hydrolysis is an acyl group.

8. A composition as claimed in claim 7 wherein the acyl group is a benzoyl, substituted benzoyl, acryloyl or substituted acryloyl group.

9. A composition as claimed in claim 7 wherein the acyl group is a benzoyl group or a substituted benzoyl group having one or more meta and/or para substituents wherein the sum of the Hammett $\sigma_m$ and $\sigma_p$ values is in the range $+0.1$ to $-1.1$.

10. A composition as claimed in claim 9 wherein the acyl group is benzoyl, optionally substituted with halogen, $C_{1-6}$ alkyl, $C_{1-6}$ alkoxy, $C_{1-6}$ alkanoyloxy, $C_{1-6}$ alkanoylamino or p-guanidino.

11. A composition as claimed in claim 8 wherein the acyl group is acryloyl, optionally substituted with $C_{1-6}$ alkyl, furyl, phenyl, or $C_{1-6}$ alkyl phenyl.

12. A derivative of an in vivo fibrinolytic enzyme as defined herein wherein the catalytic site essential for fibrinolytic activity is blocked by a group which is removable by hydrolysis such that the pseudo-first order rate constant for hydrolysis of the derivative is in the range $10^{-6}$ sec$^{-1}$ to $10^{-3}$ sec$^{-1}$ in isotonic aqueous media at pH 7.4 at 37° C. with the exception of:

(1) p-guanidinobenzoyl human plasmin, (2) p-guanidinobenzoyl streptokinase-plasminogen activator complex.

13. A derivative as claimed in claim 12 wherein the enzyme is human plasmin.

14. A derivative as claimed in claim 12 wherein the enzyme is streptokinase/human plasminogen activator complex.

15. A derivative as claimed in claim 12 wherein the enzyme is a mixture of human plasmin and streptokinase/human plasminogen activator complex.

16. A derivative as claimed in claim 12 to wherein the group which is removable by hydrolysis is an acyl group.

17. A derivative as claimed in claim 16 wherein the acyl group is a benzoyl, substituted benzoyl, acryloyl or substituted acryloyl group.

18. A derivative as claimed in claim 19 wherein the acyl group is a benzoyl group or a substituted benzoyl group having one or more meta and/or para substituents wherein the sum of the Hammett $\sigma_m$ or $\sigma_p$ values is in the range $+0.1$ to $-1.1$.

19. A derivative as claimed in claim 18 wherein the acyl group is benzoyl, optionally substituted with halogen, $C_{1-6}$ alkyl, $C_{1-6}$ alkoxy, $C_{1-6}$ alkanoyloxy, $C_{1-6}$ alkanoylamino or p-guanidino.

20. A derivative as claimed in claim 17 wherein the acyl group is acryloyl, optionally substituted with $C_{1-6}$ alkyl, furyl, phenyl, or $C_{1-6}$ alkyl phenyl.

21. p-Anisoyl human plasmin.

22. p-Anisoyl streptokinase human plasminogen activator complex.

23. A mixture of p-anisoyl human plasmin and p-anisoyl streptokinase human plasminogen activator complex.

24. A process for preparing a derivative of an in vivo fibrinolytic enzyme as claimed in claim 12 which process comprises reacting an in vivo fibrinolytic enzyme as defined herein with a blocking agent:

AB wherein A is a group which is selective for the catalytic site essential for fibrinolytic activity and which is capable of transfering from the group B to the catalytic site and B is a group which facilitates the attachment of A to the enzyme.

25. A process as claimed in claim 24 wherein the agent AB is p-nitrophenyl p-guanidinobenzoate.

26. A process for preparing a derivative as claimed in claim 11 which process comprises reacting an in vivo fibrinolytic enzyme with a compound:

EF wherein E is a locating group which is selective for the catalytic site and F is a group which is capable of transfering from the locating group to the active site.

27. A process as claimed in claim 26 wherein E is a benzoyl or substituted benzoyl group.

28. A process as claimed in claim 26 wherein E is p-amidinophenyl, or p-acetamidinophenyl.

* * * * *